United States Patent [19]
Patel et al.

[11] 4,303,343
[45] Dec. 1, 1981

[54] OPTOACOUSTIC SPECTROSCOPY OF CONDENSED MATTER IN BULK FORM

[75] Inventors: Chandra K. N. Patel, Summit, N.J.; Andrew C. Tam, Sunnyvale, Calif.

[73] Assignee: Bell Telephone Laboratories, Incorporated, Murray Hill, N.J.

[21] Appl. No.: 125,985

[22] Filed: Feb. 29, 1980

[51] Int. Cl.³ .............................................. G01N 21/01
[52] U.S. Cl. ...................................... 356/432; 250/351
[58] Field of Search ........................... 356/432; 250/351

[56] References Cited

U.S. PATENT DOCUMENTS 3,948,345  4/1976  Rosencwaig ......................... 356/432

OTHER PUBLICATIONS

Hordvik et al., "Photoacoustic Technique for Determining Optical Absorption Coefficients in Solids", *Applied Optics*, vol. 16, No. 1, Jan. 1977, pp. 101–107.
Adams et al., "Analytical Optoacoustic Spectrometry", *The Analyst*, vol. 101, No. 1199, Feb. 1976, pp. 73–85.
Farrow et al., "Piezoelectric Detection of Photoacoustic Signals", *Applied Optics*, vol. 17, No. 7, Apr. 1, 1978, pp. 1093–1098.
Bonch-Bruevich et al., "Single-and Two-Photon Spectroscopy of Liquid Media ...", *Opt. Spectrosc.*, vol. 42, No. 1, Jan. 1977, pp. 45–48.
Gutfeld et al., "20–MHz Acoustic Waves From Pulsed Thermoelastic Expansions of Constrained Surfaces", *Applied Physics Letters*, vol. 30, No. 6, Mar. 15, 1977, pp. 257–259.
Tam et al., "Ultimate Corrosion Resistant Optoacoustic Cell for Spectroscopy of Liquids", *Optics Letters*, vol. 5, No. 1, Jan. 1980, pp. 27–29.
Tam et al., "Measurement of Small Absorptions in Liquids", *Optics Letters*, vol. 4, No. 3, Mar. 1979, pp. 81–83.

*Primary Examiner*—R. A. Rosenberger
*Attorney, Agent, or Firm*—Peter V. D. Wilde

[57] ABSTRACT

Method and apparatus for high-sensitivity ($\alpha \lesssim 10^{-6} cm^{-1}$) optoacoustic (OA) spectroscopy of substantially transparent bulk condensed matter. Part of the sample to be investigated is irradiated by pulses of radiation, typically from a pulsed dye laser. The small amount of energy absorbed by the sample causes thermal expansion of the irradiated region, resulting in cylindrical stress waves being radiated from that region. These stress waves can be observed with appropriate detection means at a location remote from the source. The method is applicable to essentially transparent liquids, and solids, and to absorptive solids suspended in liquids, and the like. Possible choices of probe radiation are not only the conventional ones of visible, near UV, and near infrared electromagnetic radiation, but also, for instance, γ-rays, x-rays, vacuum UV, and far infrared. Two conditions are shown to exist that relate pulse duration, beam size, and various material parameters, observation of which results in optimization of the sensitivity of the method, and the sensitivity is typically highest for pulses having duration of about $10^{-7}$ sec–$10^{-4}$ sec.

8 Claims, 6 Drawing Figures

OPTOACOUSTIC SPECTROSCOPY OF CONDENSED MATTER IN BULK FORM

BACKGROUND OF THE INVENTION

1. Field of the Invention

This invention is in the field of absorption spectroscopy, more particularly, it pertains to optoacoustic absorption spectroscopy of condensed matter in bulk form.

2. Description of the Prior Art

Conventional optical spectroscopy techniques tend to fall into two major categories, namely, one can study and measure either the optical photons that are transmitted through the material under study, or those that are scattered or reflected from that material. During the past several years, another optical spectroscopy technique has been developed. This technique, called "optoacoustic" (OA) spectroscopy, is distinguished from the conventional techniques chiefly by the fact that even though the incident energy is in the form of optical photons, the interaction of these photons with the material under investigation is studied not through subsequent detection and analysis of photons, but rather through measurement of the energy absorbed by the material due to its interaction with the incident beam. One of the main advantages of OA spectroscopy is that in principle it enables one to obtain spectra, similar to optical absorption spectra, of any type of solid, liquid, or gaseous material. A recent review of the field of OA spectroscopy can be found in the article by Allan Rosencwaig, "Photoacoustic Spectroscopy" in *Advances in Electronics and Electron Physics*, Volume 46, Academic Press, (1978). We will restrict our discussion to OA methods that use piezoelectric transducers to detect the elastic strain waves generated by the absorption of electromagnetic energy in the sample, and that are applicable to bulk samples of condensed matter, where by "bulk samples of condensed matter," we mean solid or liquid (including suspensions and the like) samples having all three dimensions or roughly comparable magnitude, and having a total volume of the order of approximately 0.1 cm$^3$ or larger.

The principles of OA spectroscopy relevant to this application are the same whether the sample is in solid or liquid form. Typically, part of the sample volume is illuminated with an intermittent beam of essentially monochromatic electromagnetic radiation of frequency $\nu$. This illuminated sample volume we will refer to as the "source region." The matter contained in the source region absorbs radiation from the beam in proportion to $\alpha(\nu)$, the absorption coefficient for radiation of frequency $\nu$. This energy appears as heat energy in the sample and causes at least the source region to expand, resulting in elastic strain in the sample. This strain can be detected for instance by appropriately placed piezoelectric transducers, and from the transducer output $\alpha(\nu)$ can be determined.

Prior art methods of OA spectroscopy have used either chopped CW radiation, with a chopping frequency typically near 1 KHz, or pulsed laser radiation, typically involving pulses of nanosecond duration. These methods typically allowed determination of absorption coefficients larger than about $10^{-5}$ cm$^{-1}$. For instance, A. Hordvik and H. Schlossberg, *Applied Optics*, Vol. 16, pp. 101-107 (1977), describe OA apparatus that allows measurement of $\alpha(\nu) \approx 10^{-5}$ cm$^{-1}$ using CW power of a few hundred mw, resulting in power input into the sample of the order of $10^{-1}$ watt/cm$^3$ or larger, and employing chopping frequencies between 150 and 3000 Hz. On the other hand, A. M. Bonch-Bruevich et al, *Optics and Spectroscopy*, Vol. 42, pp. 45-48 (1977) describe OA measurements that use nanosecond laser pulses and have a sensitivity sufficient only to detect the absorption of $10^{-6}$ joules/pulse, resulting in a power input into the sample of the order of $10^{-6}$ watt/cm$^3$ or larger.

These prior art variants of OA spectroscopy do not utilize the full potential of the method. In the case of millisecond and longer pulses (i.e., chopped CW) the response typically is reduced due to effects of thermal diffusion, and, in any case, it can be shown that such long pulses result in reduced sensitivity of the measurement. On the other hand, it is also easy to show that nanosecond pulses are nonoptimal because they typically result in a reduced response due to destructive interferences at the transducer between signals from different parts of the source region.

DESCRIPTION OF THE INVENTION

We have discovered that, by properly choosing the pulse length, it is possible to avoid the above-mentioned deficiencies of the prior art methods of OA spectroscopy, resulting in substantially increased sensitivity and accuracy, with decreased sample heating. We have achieved the capability of measuring absorptions of $\sim 10^{-7}$ cm$^{-1}$ or less in samples of about 1 cm$^3$ volume, with pulses of about $10^{-3}$ joules.

We are generally interested in the case of pulsed probe radiation, with the pulse length $\tau_p \ll$ the time between successive pulses. In the visible part of the spectrum, scannable flash-lamp pumped dye lasers can advantageously be used as sources of probe radiation, but, of course, other means of generating the appropriate pulses exist and may be preferable for certain measurement situations. Although this disclosure is primarily in terms appropriate to visible electromagnetic radiation, our invention is not thus limited, and $\gamma$-rays, x-rays, vacuum UV, UV, and infrared probe radiation can be used as well. In principle, even particle pulses could be used, although most of the commonly available particles, such as electrons, positrons, protons, and $\alpha$-particles interact strongly with ordinary matter and thus have an absorption length that is undesirably short to make use of the method disclosed herein advantageously. On the other hand, neutrons and neutrinos interact much more weakly with matter, and therefore our invention can, in principle, be employed with these particles. Furthermore, our invention is most suitable to the measurement of bulk samples in which the absorption of the probe radiation is small, i.e., substantially "transparent" samples. For purposes of this disclosure, we consider a sample transparent at the frequency $\nu$ if the absorption $\alpha(\nu) \lesssim 10^{-2}$ cm$^{-1}$, since in such a case the intensity of probe radiation is, for practical purposes, uniform over the length of the illuminated sample volume (the "source region"). However, the above does not mean that only transparent substances can be measured by our method. If the absorption of a highly absorbing solid is to be determined, one can, for instance, prepare a dilute suspension of the powdered solid in a transparent liquid, and measure the absorption of the suspension, thereby determining $\alpha(\nu)$ of the absorbing solid.

Figure 1:
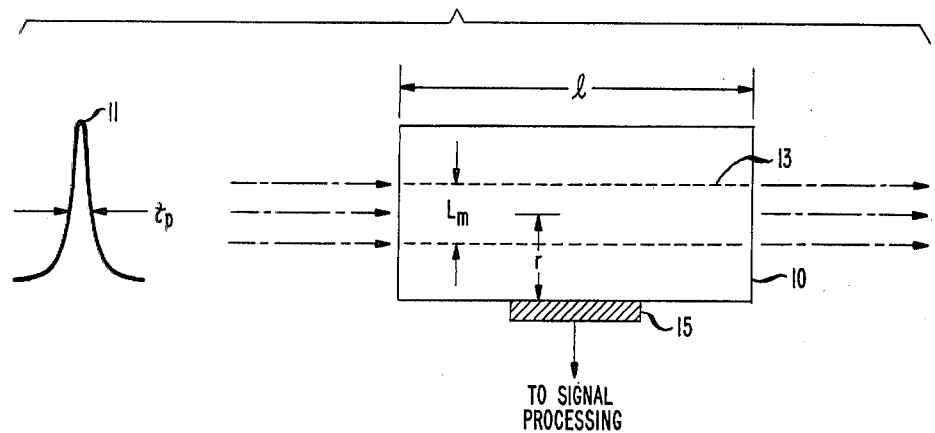
FIG. 1 shows schematically a sample and probe beam.

The theory of CA pulse generation has been treated by several authors (see, for instance, C. K. N. Patel and A. C. Tam, *Reviews of Modern Physics*, (to be published), and we will here concentrate on those results that are necessary to understand the improvements in OA spectroscopy disclosed by us. FIG. 1 illustrates the experimental situation we will discuss. Part of medium 10 is irradiated with pulsed probe radiation, the pulses 11 having pulse duration $\tau_p = 2\tau$. The irradiated part of the medium 13, the source region, has maximum cross-sectional dimension $L_m$, and is 1 cm long. A transducer 15, typically a piezoelectric transducer, is in intimate contact with the medium, at a distance r from the center of the source region.

If a thin cylinder of liquid (or solid if only compressional acoustic waves are considered) of length 1 and absorption coefficient $\alpha$, with $\alpha l << 1$, is irradiated by a probe pulse of duration $\tau_p = 2\tau$ and pulse energy $E_o$ then, because of the restriction to weak absorption, the thin cylinder will absorb radiation uniformly over its length, and the problem is essentially two-dimensional. Unless radiative decay channels exist, all the radiation energy absorbed by the material within the thin cylinder will eventually appear as heat energy, causing a pulse-like thermal expansion of the cylindrical volume, resulting in cylindrical compressional acoustic waves propagating outwards from the cylindrical source region, which can be detected by means of an appropriate transducer. By a "thin" cylinder, we mean a cylinder having a largest cross-sectional dimension $L_m \lesssim \tau_p$, where v is the appropriate acoustic phase velocity. This condition assures that all parts of the source region contribute inphase to the signal at the transducer, and we will refer to it as the "phase condition." Since in most solids and liquids v is typically of the order of $10^5$ cm sec$^{-1}$, we see that for pulse lengths of $10^{-7}$ sec the phase condition is fulfilled for beam sizes of about $10^{-2}$ cm, and that for longer pulses it is increasingly easy to obey.

The cross-sectional dimensions of the cylinder should also be chosen to obey $L_m << \lambda_{diff}$, where $\lambda_{diff} = (4\tau_p D)^{\frac{1}{2}}$ is the thermal diffusion length during the pulse duration $\tau_p$, and D is the thermal diffusivity of the medium, typically $\sim 10^{-3}$ cm$^2$ sec$^{-1}$ for most liquids. This condition, to be referred to as the "adiabatic condition," insures that the source region has a well-defined boundary coincident with the boundary of the irradiated volume, and, more importantly, that the response of the medium to the radiation pulse is pulse-like and truly optoacoustic. For $\tau_p = 10^{-6}$ sec and shorter, it is apparent that $\gamma_{diff} \lesssim 10^{-3}$ cm and the adiabatic condition is met for all practical probe beams. The same conclusion does not necessarily follow for long probe pulses, however, since for $\tau_p = 10^{-2}$ sec, for instance, $\lambda_{diff} \approx 10^{-2}$ cm, and this is comparable to possible $L_m$.

If these two conditions are obeyed simultaneously, then the response of the medium will be strictly optoacoustic, with no thermal effects present in the detected signal, and the signal will be of maximum amplitude, for reasons that will become apparent presently.

Figure 2:
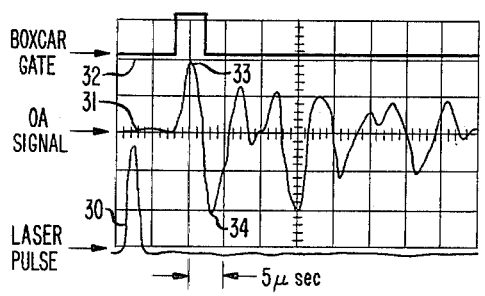
FIG. 2 reproduces oscilloscope traces as observed in an OA experiment.

The results below can easily be demonstrated analytically for probe pulses of Gaussian shape (see Patel and Tam, ibid), but they are also approximately true for non-Gaussian pulses. The acoustic pressure at a distant observation point can be expressed as a time integral, the integrand containing a "source" term, namely the time derivative of the velocity of thermal expansion of the source region. The source term has the largest amplitude at $|t'| \approx 0.7\tau$, and vanishes rapidly at large $|t'|$. From this, one can expect that the acoustic pressure at the observation point r cm from cylindrical source region will be of largest magnitude at $t_\pm \approx r/v \pm 0.7\tau$. Evaluation of the integral shows that the acoustic signal at the observation point consists of a compression pulse at time $t_-$, followed by a rarefaction pulse of almost equal magnitude at $t_+$, with the time interval between the two pulses being approximately the duration of the probe pulse. FIG. 2 shows that this is indeed observed. Oscilloscope trace 30 shows the pulse of probe radiation, a laser pulse of $\tau_p \approx 2$ µsec. Trace 31 is the amplified output of the piezoelectric transducer used to observe the OA signal. Peak 33 is the compression pulse, the first response of the medium to the probe pulse to arrive at the transducer, after a travel time of approximately 7 µsec. Peak 34 is the rarefaction pulse, about 3 µsec after the compression pulse. The later structure in 31 is due primarily to transducer ringing, and does typically not contain useful information.

It is the form of the acoustic response, namely, a compression pulse followed by a rarefaction pulse approximately $\tau_p$ later that makes advantageous adherence to the phase condition since, if the condition is violated, the two pulses from different parts of the source region can interfere destructively, thereby decreasing the observed signal and thus the sensitivity of the method.

Above we have discussed the necessary relationships between pulse length $\tau_p$ and maximum cross-sectional beam dimension $L_m$, and have shown that generally a regime exists in which both phase condition and adiabatic condition can be satisfied simultaneously. For typical materials and practical beam dimensions, this corresponds to $\tau_p$ between approximately $10^{-7}$ sec and approximately $10^{-2}$ sec. We will now show that further considerations typically reduce further the most advantageous pulse length regime. In particular, we will show that the best mode of carrying out OA spectroscopy involves a pulsed source having pulse lengths from about 0.1 µsec to less than about 100 µsec.

Theory shows that the maximum acoustic pressure due to a probe pulse of energy $E_o$ and duration $2\tau$ is proportional to $E_o \tau^{-3/2}$. Thus, in order to maximize the OA signal, it is advantageous to either increase the energy per pulse or decrease the pulse length. The former will lead not only to an increased signal but also to increased heating of the sample, and thus be undesirable beyond a certain point. On the other hand, shortening the pulse duration not only is more effective in increasing the signal (due to the $-3/2$ power dependence of $\tau$) but also avoids undesirable thermal effects on the sample.

As was shown above, the phase condition imposes a lower limit on $\tau_p$ of about $10^{-7}$ sec. Flash lamp pulsed lasers typically have $\tau_p \sim 10^{-6}$ sec, and we have found this to be a very convenient pulse length. An advantageous way to practice our invention employs a pumped dye laser having pulse lengths of about $10^{-6}$–$10^{-5}$ sec and beam diameter typically of the order of $10^{-1}$ cm, but the invention can be usefully practiced over the pulse length regime from about $10^{-7}$ sec to $10^{-4}$ sec, with the upper limit determined by the decreasing sensitivity of the method with increasing pulse length.

Because of the increased sensitivity of OA measurements according to our teachings, it is possible to reduce the energy input into the sample, thereby permitting essentially isothermal measurements, as well as making possible OA measurements at very low temperatures, where heat load has to be minimized. One of the relevant quantities for comparing thermal effects on the sample as a whole is the power absorbed/unit sample volume, Q.

$$Q = \alpha l E_o \nu_R / V$$

where $\alpha$, $l$, $E_o$ have been defined above, $\nu_R$ is the pulse repetition rate, and V is the sample volume. It is desirable to design measurements such that $Q \lesssim 10^{-6}$ watt/cm$^3$, the best value achieved in the prior art. This will lead to typical temperature rises $\Delta T \lesssim 10^{-4}$ K.

Figure 3:
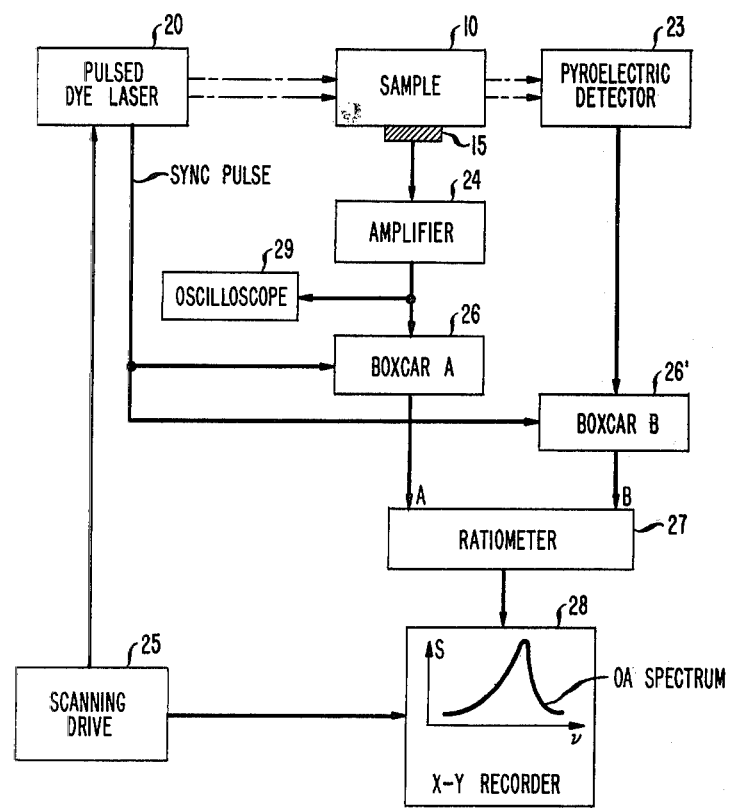
FIG. 3 illustrates, in block diagram form, possible OA instrumentation.

FIG. 3 shows in block diagram form a possible instrumentation scheme for OA spectroscopy of bulk material. Pulsed light source 20, typically a pulsed dye laser, emits light pulses at a rate that is controlled in some appropriate manner, and of a frequency determined by scanning mechanism 25. The probe pulse passes through the transparent sample 10, and then to pyroelectric detector 23. The output of transducer 15 is fed to low-noise bandpass preamplifier 24. Because of the high electrical impedance of most piezoelectric transducers a relatively high-quality preamplifier having high input impedance, low noise figure, and being physically in close proximity to the transducer is desirable. For instance, we have found a commercial preamplifier, Ithaco Model 143F, to be satisfactory. The signal is then fed to boxcar integrator 26, as well as to oscilloscope 29 for direct viewing. As is well known, a boxcar allows the time-gating of the signal portion to be integrated, thereby permitting the use of any particular small portion of a complicated signal. We found this feature to be very convenient, but, of course, useful results could be obtained without it. The output of pyroelectric detector 23 is fed to a second boxcar integrator 26', and ratiometer 27 serves to form the ratio A/B, that is, the ratio between the integrated OA signal and the integrated light pulse intensity. This ratio is then recorded by recorder 28 as a function of frequency $\nu$, and the resulting curve is the normalized absorption of the sample 10 as a function of frequency. Those skilled in the art will be easily able to modify the instrumentation scheme shown in FIG. 3 to fit particular requirements that may arise. For instance, it would be an obvious step to replace ratiometer 27 by a microprocessor or computer. As an example of possible instrumentation, we have used a commercial scannable flash lamp pumped dye laser that produced about 1 mJ of energy in about 1 $\mu$sec duration pulses, at a laser bandwidth of about 2 cm$^{-1}$. A useful pulse frequency is of the order of 10 pulses per second. The bandwidth of the light used depends on the desired spectral resolution, and could vary from perhaps 0.1 cm$^{-1}$ for some low temperature investigations to perhaps about 100 cm$^{-1}$. One possible pyroelectric detector is a coated lithium niobate detector, such as, for instance, Laser Precision Model 2050S.

Figure 4:
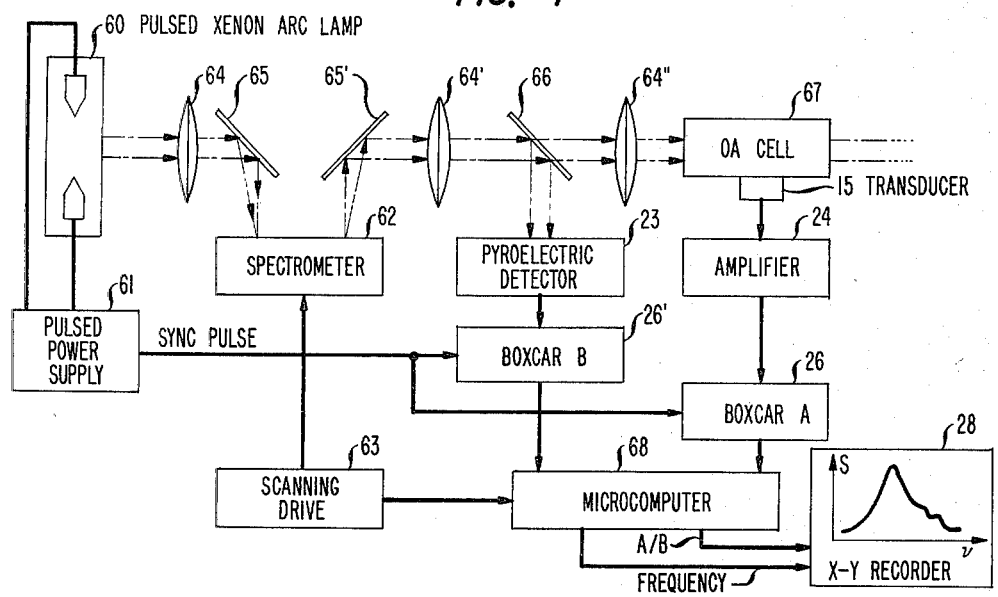
FIG. 4 illustrates, in block diagram form, another possible OA instrumentation scheme.

However, the pulsed light source does not have to be a laser. For instance, it could be a pulsed arc lamp, or even a continuously emitting light source together with an appropriate chopping device, provided the requirements on pulse length can be fulfilled. As an example, FIG. 4 shows in block diagram form a possible instrumentation scheme for OA spectroscopy of bulk materials using a pulsed source of broad band radiation. Pulsed arc lamp 60, typically a high pressure xenon arc lamp, emits broad band light pulses approximately 1 $\mu$sec long, at a pulsed repetition frequency which is variable from about 1 pulse per second to about 100 pulses per second. Power supply 61 controls the pulsed arc lamp operation and also supplies a synchronizing pulse to boxcars 26 and 26'. Spectrometer 62 typically uses a grating as dispersion element, and serves as a narrow-banding device. Scanning drive 63 determines the center frequency of the narrow band pass output of 62 and also conveys that information to computer 68. Focusing systems 64, 64', 64" and mirrors 65 and 65' focus the radiation onto the entrance slit of 62 and into OA cell 64 to which transducer 15 is attached. Analogously to the scheme shown in FIG. 3, the output from the transducer is amplified by amplifier 24, then fed to boxcar 26 with the boxcar gate typically set to admit only a selected portion of the transducer signal. Beam splitter 66 diverts a small fraction of the probe beam intensity into pyroelectric detector 23, whose output signal is integrated using boxcar 26'. The outputs of boxcars 26 and 26' are fed into microcomputer 68 which performs simple data processing operations to normalize the OA signal, and permit X-Y recorder 28 to plot the normalized opto-acoustic signal as a function of frequency. With typical currently available pulsed xenon arc lamps, it is possible to obtain probe pulses of duration of the order of one microsecond and energy of the order of 1 millijoule in the narrow band pass output from the spectrometer over the entire visible and near-infrared region.

FIG. 2, discussed above, shows a reproduction of three oscilloscope traces, with trace 30 corresponding to the output of pyroelectric detector 23 of FIG. 3, trace 31 corresponding to the amplified output of transducer 15 of FIG. 3, and trace 32 showing the position in time and the width of the gate of boxcar 26 from that figure. The relevant features of the three oscilloscope traces were discussed earlier, we only want to mention here that by properly positioning the boxcar gate one can, for instance, look at the initial, i.e., compressional, OA pulse only, thereby avoiding all difficulties due to scattered light and transducer ringing. The gate positioned as shown in FIG. 2 would accomplish this.

Figure 5:
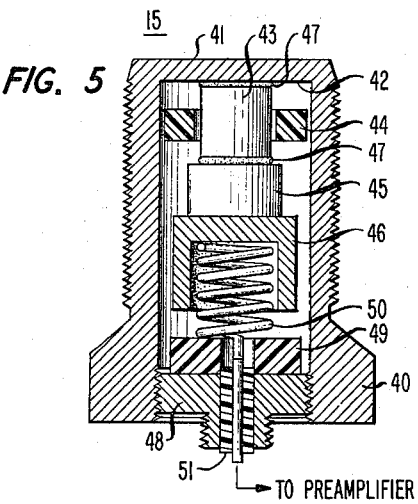
FIG. 5 shows schematically and in cross section a possible transducer assembly, and FIG. 6 gives an example of results obtained by OA utilizing the improvement disclosed herein.

In FIG. 5, we show the details of a transducer assembly that we have found useful, but of course, many equivalent or similar designs are possible. Housing 40 is fabricated from stainless steel, with the membrane between highly polished sufaces 41 and 42 being about 1 mm thick. Transducer 43 is kept centered by a teflon ring 44 and forced against the membrane by means of spring 50, which is restrained laterally by copper housing 46, to which is soldered lead absorber 45. Very thin layers of grease 47 between membrane surface 42 and transducer 43 as well as between the transducer and the absorber 45 serve to improve acoustical coupling. Appropriate deformation of the piezoelectric transducer results in the appearance of a voltage between the metallized plane surfaces of the transducer, i.e., the surfaces adjacent to membrane surface 42 and lead absorber 45. Copper bronze spring 50 is in electrical contact with a miniature coaxial connector 48 and thus completes the conductive path between the transducer and the connector, making any electrical signal produced by the transducer available for further processing. Spring 50 pushes against dielectric ring 49, which, together with insulator 51, prevents short-circuiting of the output signal. As can be seen, the transducer assembly forms an essentially complete metallic enclosure, thereby reducing electromagnetic interference with the transducer signal. A further advantage is the relatively large thermal mass of the steel housing 40, which reduces thermal noise due to scattered light that reaches the transducer assembly. Polished surface 41 not only makes good acoustic coupling to the sample possible but also serves to reflect scattered light incident on it, thereby further reducing thermal noise. Absorber 45 is a lead disc because lead has relatively large ultrasonic absorption, thus serving to reduce undesirable effects due to reflected ultrasonic waves. We have used commercially available cylindrical ceramic transducers, poled and dimensioned to respond predominantly to compressional waves of about 1 MHz. However, a wide variety of different materials, shapes, mode dependencies, and resonant frequencies would be equally practical, and any choice would obviously be dictated by the particulars of the measurement planned. For instance, for some applications, measurements at much higher or much lower frequencies might be of interest, whereas for other applications it might be desirable to use a broadband transducer that is responsive to many frequencies.

Figure 6:
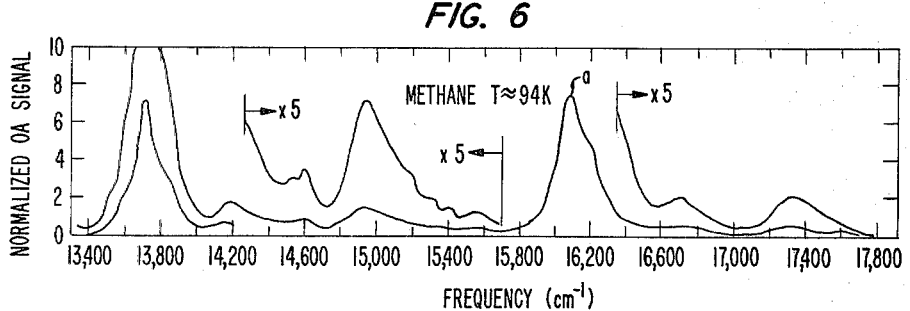

To illustrate the capabilities of OA spectroscopy that incorporates the improvements disclosed herein, we show in FIG. 5 results of an actual measurement, namely, the normalized OA signal of liquid methane at 94° K. from 13,300 $cm^{-1}$ to 17,800 $cm^{-1}$, i.e. the absorption spectrum for optical radiation between about 7500 Å and about 5600 Å. The spectral resolution, typically 2 $cm^{-1}$, is much smaller than the observed widths of the clearly recognizable absorption features, which is typically 200–300 $cm^{-1}$. The peak absorption coefficient for the absorption feature marked a, at approximately 16,090 $cm^{-1}$, is about $3 \times 10^{-3}$ $cm^{-1}$. From the signal-to-noise ratio seen on this figure it is evident that our ability to measure very small absorptions, even at low temperatures, exceeds the prior art limit of about $10^{-6}$ $cm^{-1}$. The data shown in FIG. 6 have been obtained by using a time constant of 1 sec for a resolution of about 1 $cm^{-1}$. They contain a wealth of information, a discussion of which is however not necessary for an appreciation of the quality of the results obtainable by our improved method of OA spectroscopy. However, it should be pointed out that previous measurements of absorption of liquid methane were able to detect only peak a, with a signal-to-noise ratio of about 5 to 1. There are, however, previous measurements of absorption spectra of gaseous methane at pressures of 20 atmospheres, using path lengths of the order of 1 km, which show many of the features we see for liquid methane at 94 K. using a sample cell path length of only 1 cm. We see that the OA spectroscopy technique described here is a very powerful one for measuring weak spectra, in this particular case at a temperature as low as 94 K. The technique can be extended for operation at temperatures as low as liquid helium temperatures. Measurements can also be carried out at very high temperatures where the typical limiting feature is the disappearance of piezoelectricity when transducers reach temperatures above the Curie temperature of the transducer material.

As we have already indicated above, our method is applicable to transparent bulk and solid samples, to suspensions of absorbing solids in transparent liquids, and the like. A solid sample is typically shaped as indicated in FIG. 1, with the entrance and exit surfaces of the radiation parallel to each other, and prepared to reduce scattering of the radiation. The transducer would typically be attached directly to the sample, in a position similar to that shown in FIG. 1. However, if desired, a relatively nonabsorbing intermediary material, such as, for instance, a quartz delay rod, could be interposed between sample and transducer. A liquid sample must, of course, be contained within a sample cell, and many such cells have been described in the literature. A particularly simple and noncontaminating one is described by A. C. Tam and C. K. N. Patel in *Optics Letters*, Vol. 5(1), pp. 27–29 (January 1980). Variations in cell construction or sample shape as well as in other experimental details would of course not affect the scope of our disclosure and claims.

We claim:

1. An improved method for optoacoustic spectroscopy of a bulk sample of relatively transparent condensed matter comprising
    (a) irradiating at least a part of the sample, the source region, with a pulsed beam of radiation of frequency $\nu$ and pulse length $\tau_p$, with pulse rate $\nu_R$,
    (b) limiting the beam dimensions to a maximum cross-sectional dimension of the source region $L_m$, and
    (c) detecting elastic waves generated in the sample that have propagated to the detecting means substantially only through condensed matter,
   wherein the improvement comprises
    (d) adjusting $\tau_p$ to be between about $10^{-7}$ and $10^{-4}$ seconds.
    (e) adjusting $\nu_R$ to be much less than about $\tau_p^{-1}$, and
    (f) adjusting the beam such that $L_m \lesssim \nu \tau_p$, and simultaneously $L_m$ to be much greater than about $(4\tau_p D)^{\frac{1}{2}}$, where
   $\nu$ is the phase velocity in the sample of elastic compressional waves, and
   D is the thermal diffusivity of the sample material.

2. Method according to claim 1, further comprising adjusting the energy in the pulse $E_o$ that $(\alpha(\nu)lE_o\nu_R/V) \lesssim 10^{-6}$ watt/$cm^3$, where $\alpha(\nu)$ is the absorption coefficient of the sample,
   l is the length of the source region in the sample,
   $\nu_R$ is the pulse rate, and
   V is the sample volume.

3. An improved apparatus for optoacoustic spectroscopy of a bulk sample of relatively transparent condensed bulk matter comprising
    (a) means for irradiating at least a part of the sample, the sample source region, with a pulsed beam of radiation of frequency $\nu$ and pulse length $\tau_p$, with pulse rate $\nu_R$,
    (b) means for limiting the beam dimensions to a maximum cross-sectional dimension of the source region $L_m$, and
    (c) means for detecting elastic waves generated in the sample that have propagated to the detecting means substantially only through condensed matter,
   wherein the improvement comprises (d) means for adjusting $\tau_p$ to be between about $10^{-7}$ and $10^{-4}$ seconds, (e) means for adjusting $\nu_R$ to be much less than about $\tau_p^{-1}$, and (f) means for adjusting the beam-dimension-limiting means such that $I_m \lesssim v\tau_p$, and simultaneously $L_m$ to be much greater than about $(4\tau_p D)^{\frac{1}{2}}$, where v is the phase velocity in the sample of elastic compressional waves, and D is the thermal diffusivity of the sample material.

4. Aparatus according to claim 3, further comprising means for adjusting the energy in the pulse $E_o$ such that $(\alpha(\nu)lE_o\nu_R/V) \lesssim 10^{-6}$ watt/cm$^{-3}$, where $\alpha(\nu)$ is the absorption coefficient of the sample, l is the length of the source region in the sample, $\nu_R$ is the pulse rate, and V is the sample volume.

5. Apparatus according to claim 3 wherein the irradiating means comprise a pulsed laser.

6. Apparatus according to claim 3 wherein the irradiating means comprise a pulsed arc lamp.

7. Apparatus according to claim 5 wherein the pulsed laser is a dye laser having a pulse length of the order of $10^{-6}$ sec and a repetition rate of the order of 10 sec$^{-1}$.

8. Apparatus according to claim 3 wherein the radiation used is $\gamma$-, X-, vacuum UV, UV, infrared, or far infrared radiation.

* * * * *

UNITED STATES PATENT AND TRADEMARK OFFICE
CERTIFICATE OF CORRECTION

PATENT NO. : 4,303,343

DATED : December 1, 1981

INVENTOR(S) : Chandra K. N. Patel and Andrew C. Tam

It is certified that error appears in the above—identified patent and that said Letters Patent is hereby corrected as shown below:

Column 1, line 49, "This" should read --The--.
Column 3, line 14, "CA" should read --OA--. Column 3, line 24, "1" should read --$\ell$--. Column 3, line 29, "1" should read --$\ell$--. Column 3, line 30, "$\alpha 1<<1$" should read --$\alpha\ell<<1$--.
Column 3, line 43, "$L_m \stackrel{<}{\sim} \tau_p$" should read --$L_m \stackrel{<}{\sim} v\tau_p$--.
Column 3, line 54, "$L_m<<\lambda_{diff}$" should read --$L_m>>\lambda_{diff}$--.

Column 4, line 16, after "from" add --the--. Column 5, line 22, "1," should read --$\ell$,--. Column 6, line 21, "compouter" should read --computer--. Column 8, line 48, "1" should read --$\ell$--. Column 8, line 51, "1" should read --$\ell$--.
Column 9, line 6, "$I_m$" should read --$L_m$--.
Column 9, line 13, "1" should read --$\ell$--. Column 10, line 1, "1" should read --$\ell$--.

Signed and Sealed this

Eleventh Day of May 1982

[SEAL]

Attest:

GERALD J. MOSSINGHOFF

Attesting Officer    Commissioner of Patents and Trademarks